United States Patent
Kuramochi

(10) Patent No.: US 10,729,591 B2
(45) Date of Patent: Aug. 4, 2020

(54) ABSORBENT ARTICLE

(71) Applicant: Daio Paper Corporation, Shikokuchou-shi, Ehime (JP)

(72) Inventor: Mihoko Kuramochi, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 350 days.

(21) Appl. No.: 15/022,422

(22) PCT Filed: Sep. 9, 2014

(86) PCT No.: PCT/JP2014/073732
§ 371 (c)(1),
(2) Date: Mar. 16, 2016

(87) PCT Pub. No.: WO2015/045842
PCT Pub. Date: Apr. 2, 2015

(65) Prior Publication Data
US 2016/0220421 A1    Aug. 4, 2016

(30) Foreign Application Priority Data
Sep. 30, 2013  (JP) .................................. 2013-204783

(51) Int. Cl.
*A61F 13/15* (2006.01)
*A61F 13/47* (2006.01)
(Continued)

(52) U.S. Cl.
CPC ........ *A61F 13/15203* (2013.01); *A61F 13/47* (2013.01); *A61F 13/51104* (2013.01);
(Continued)

(58) Field of Classification Search
CPC ...... A61F 13/51104; A61F 2013/15447; A61F 2013/15463
See application file for complete search history.

(56) References Cited

U.S. PATENT DOCUMENTS 4,041,951 A * 8/1977 Sanford ............ A61F 13/51305
604/375
6,417,427 B1 * 7/2002 Roxendal .......... A61F 13/53713
604/378
(Continued)

FOREIGN PATENT DOCUMENTS

JP    2006-239127         9/2006
JP    2006305044 A  * 11/2006
(Continued)

OTHER PUBLICATIONS

English Translation of "JP 2006305044", https://worldwide.espacenet.com, Oct. 12, 2018.*
(Continued)

*Primary Examiner* — Timothy A Stanis
*Assistant Examiner* — Cana A Gallegos
(74) *Attorney, Agent, or Firm* — Norris McLaughlin, P.A.

(57) ABSTRACT

To provide excellent skin touch feeling, a compression resistant and durable concavo-convex shape providing an uneven feeling, and excellent absorption performance, a sanitary napkin is provided that includes an absorber interposed between a permeable front surface sheet embossed into a concavo-convex shape and a back surface sheet and a hydrophilic third sheet disposed between the permeable front surface sheet and the absorber. The permeable front surface sheet is a laminate structure that includes a fine fiber skin contact surface layer made of fine fibers having a fineness of less than 2.0 dtex and a crimped fiber layer laminated on the non-skin contact surface of the fine fiber layer and the crimped fibers have a fineness of from 3.0 to 5.0 dtex.

1 Claim, 5 Drawing Sheets

(51) Int. Cl.
*D04H 1/4374* (2012.01)
*A61F 13/511* (2006.01)
(52) U.S. Cl.
CPC .. *D04H 1/4374* (2013.01); *A61F 2013/15463* (2013.01); *A61F 2013/51178* (2013.01)

(56) References Cited

U.S. PATENT DOCUMENTS

| | | | | |
|---|---|---|---|---|
| 7,102,054 | B1* | 9/2006 | Cree | A61F 13/51305 604/367 |
| 7,569,264 | B2* | 8/2009 | Toyoshima | A61F 13/5116 428/156 |
| 8,748,692 | B2* | 6/2014 | Suzuki | A61F 13/51104 604/380 |
| 2004/0142151 | A1* | 7/2004 | Toyoshima | D04H 3/14 428/172 |
| 2009/0004435 | A1* | 1/2009 | Hanao | A61F 13/53 428/156 |
| 2011/0166540 | A1* | 7/2011 | Yang | A61F 13/15203 604/367 |
| 2011/0313385 | A1* | 12/2011 | Hammons | A61F 13/4756 604/378 |
| 2012/0157950 | A1* | 6/2012 | Geilich | A61F 13/5116 604/366 |

FOREIGN PATENT DOCUMENTS

| | | | |
|---|---|---|---|
| JP | 2006305044 | A * | 11/2006 |
| JP | 2009-050538 | | 3/2009 |
| JP | 4566059 | | 8/2010 |
| JP | 4566059 | B2 * | 10/2010 |
| JP | 2011-015707 | | 1/2011 |
| JP | 2012-239720 | | 12/2012 |

OTHER PUBLICATIONS

English Translation of "JP 2006305044", https://worldwide.espacenet.com, Oct. 12, 20108 (Year: 2006).*

* cited by examiner

[Fig. 1]
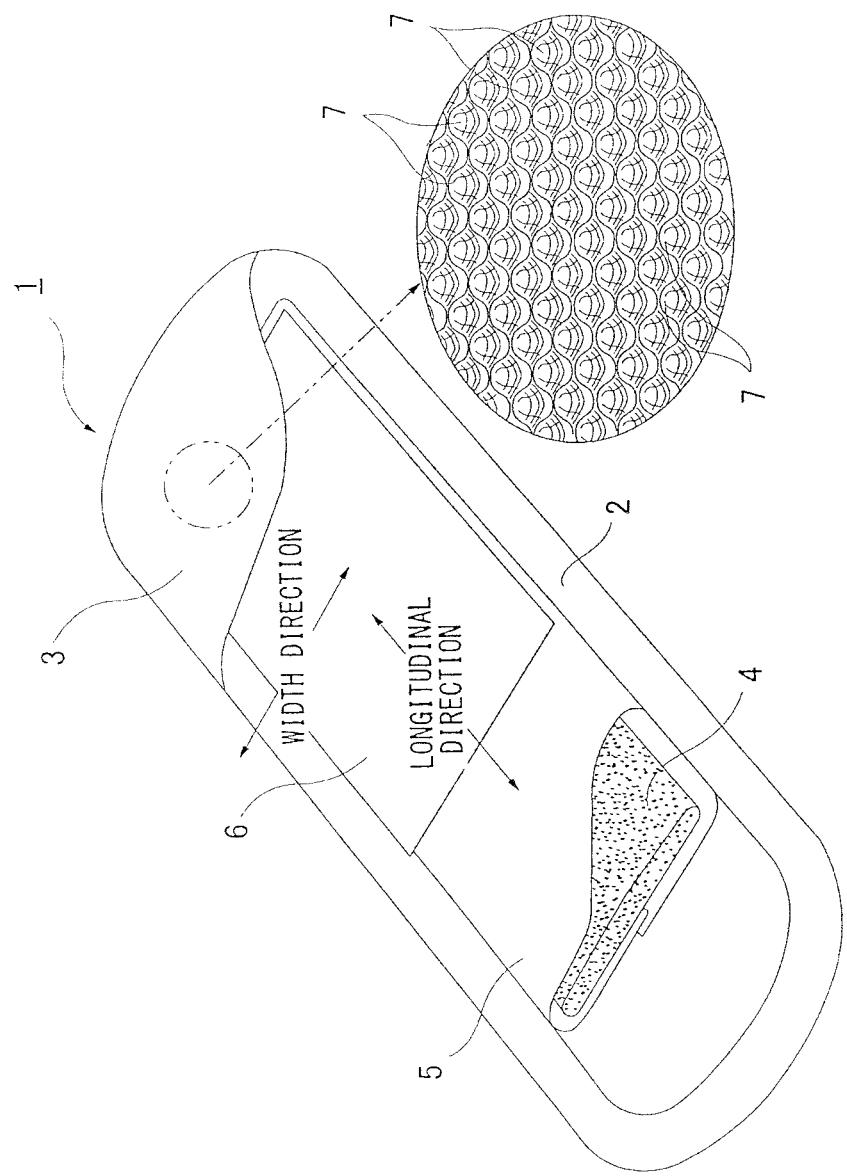

[Fig. 2]
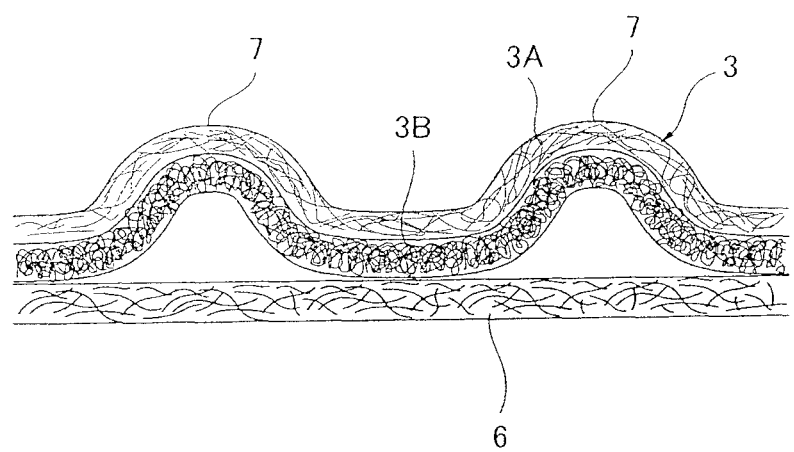

[Fig. 3]
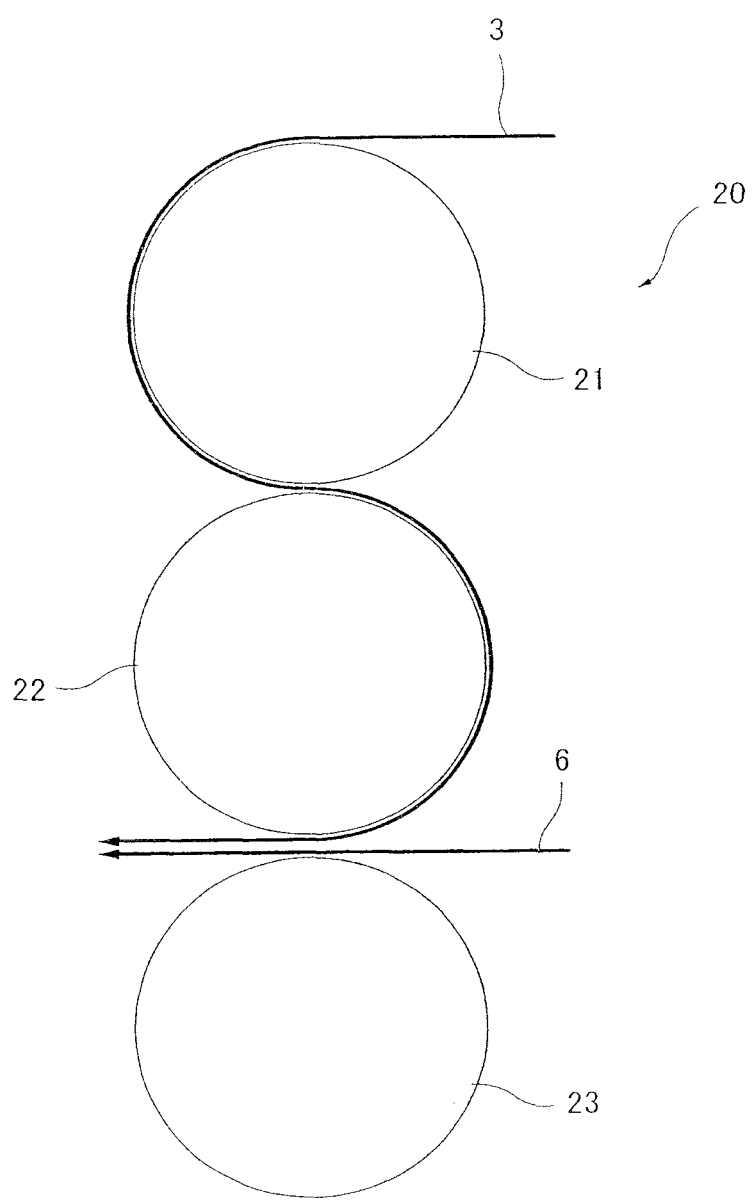

[Fig. 4]
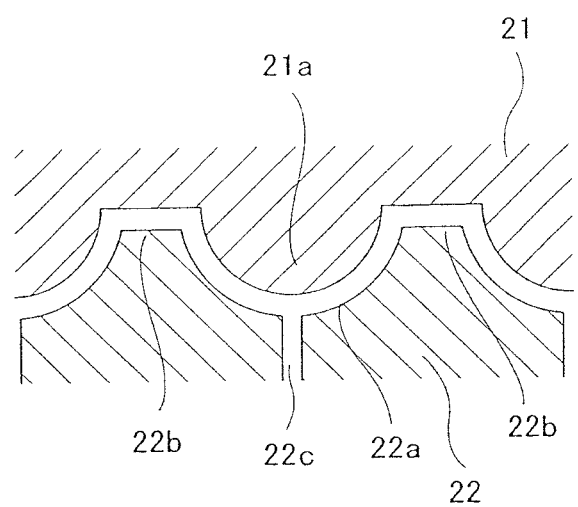

[Fig. 5]
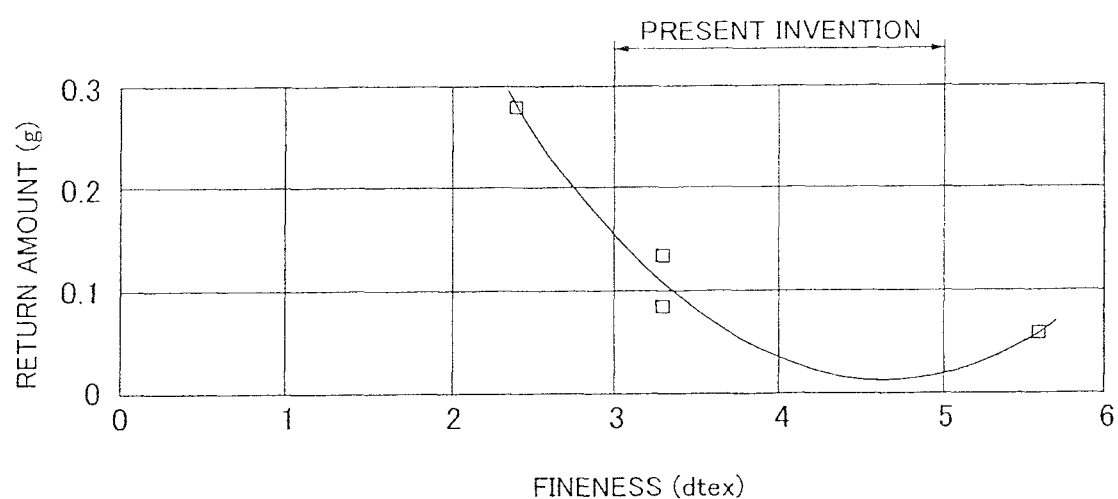

ABSORBENT ARTICLE

BACKGROUND OF THE INVENTION

The present invention relates to an absorbent article such as sanitary napkins, panty liners, incontinence pads, and disposable diapers for absorbing menstrual blood, vaginal discharges, urine and the like, and particularly to an absorbent article provided with a concavo-convex pattern on a permeable front surface sheet.

Front surface materials for absorbent articles, in which an appropriate emboss pattern is imparted in accordance with various objects such as suppressing a wet feeling by reducing a contact area with skin, or imparting texture to improve the feeling of contact with the skin have been commercialized. As materials of this kind, for example, the following Japanese Patent No. 4566059 and JP 2009-50538 A and the like can be cited.

In Japanese Patent No. 4566059, an absorbent article that includes a permeable front surface sheet, an impermeable or water-repellent back surface sheet, and an absorber located between the both sheets, and is provided with an intermediate sheet between the front surface sheet and the absorber is disclosed. The permeable front surface sheet includes a first layer that forms a skin contact surface, and a second layer that is adjacent to the first layer and disposed on the absorber side. The first layer is made of a fiber that has a fineness of 2.2 dtex or less and hydrophilicity that is not susceptible to decrease due to liquid permeation. The second layer is constituted of a fiber less fine than the constituent fiber of the first layer and contains a fiber of which hydrophilicity is not susceptible to decrease due to liquid permeation and a fiber of which hydrophilicity is susceptible to decrease due to the liquid permeation. The intermediate sheet includes a third layer facing the front surface sheet and a fourth layer that is adjacent to the third layer and facing the absorber. The constituent fiber of the third layer is less than the fineness of constituent fiber of the fourth layer. The fineness of the constituent fiber of the third layer is equal to or less than the fineness of the constituent fiber of the second layer. The constituent fiber of the fourth layer is finer than the constituent fiber of the second layer. (Of course, the finer the fiber the lower its dtex, and the less fine the fiber, the higher its dtex.) The constituent fibers of the third layer and fourth layer are a fiber of which hydrophilicity is not susceptible to decrease due to liquid permeation, and an entirety or a part of the constituent fiber of the third layer is formed of a solid crimped fiber.

Further, in JP 2009-50538 A, a sheet for an absorbent article in which a first sheet having an outside layer and an inside layer is intermittently joined to a second sheet at the inside layer is disclosed. In Japanese Patent No. 4566059 projected part protruding to the first sheet side formed between joining parts is connected to the sheet for an absorbent article, and a fiber that constitutes the outside layer of the first sheet is a fiber finer than the fiber that constitutes the inside layer.

In the absorbent article described in Japanese Patent No. 4566059, by imparting a gradient of fineness and a gradient of degree of durability of hydrophilicity to the front surface sheet and the intermediate sheet each formed into a two-layered structure, an excellent liquid return prevention property is imparted and the feeling on the skin is improved. However, the absorbent article is not formed into a structure that can maintain a concavo-convex shape of an emboss pattern when the emboss pattern is imparted to the front surface sheet.

In the same manner also in the sheet for absorbent article described in JP 2009-50538 A, it is disclosed to impart a gradient of fineness to an inside layer and an outside layer to impart comfortable touch feeling or the like on the skin. However, while a projected part collapses or deforms due to body pressure or the like to deteriorate feeling on the skin ("skin touch feeling"), there is no disclosure of a technology for maintaining the shape retention property of projected part or for making it difficult to deform.

SUMMARY OF THE INVENTION

An absorbent article that, while maintaining the shape retention property of a concavo-convex shape on a surface, combines cushioning and, hence, comfort, when in contact with skin and an uneven skin-facing surface which minimizes contact with skin, and absorption performance such as a return amount of body fluid in a balanced manner has not been developed.

A principal object of the present invention is to provide an absorbent article in which a stable concavo-convex shape made by surface emboss processing is provided, the skin touch feeling or "the uneven feeling" (i.e., the feeling provided by an irregular skin-facing surface only portions of which contact the skin due to irregularity of the surface) is made excellent and absorption performance is improved.

As the first aspect of the invention for attaining the above-described object, an absorbent article that includes an absorber interposed between a permeable front surface sheet and a back surface sheet and a hydrophilic sheet disposed between the permeable front surface sheet and the absorber is provided, in which the permeable front surface sheet is formed of a laminate structure that includes a fine fiber layer made of fine fibers that constitutes a skin contact surface and has a fineness of less than 2.0 dtex, and a crimped fiber layer made of crimped fibers and that is adjacently laminated on a non-skin surface side of the fine fiber layer and has the fineness of from 3.0 to 5.0 dtex, and is embossed into a concavo-convex shape formed of a multiplicity of raised parts protruding to a skin side.

According to the first aspect of the invention, the permeable front surface sheet is formed of a laminate structure that includes a fine fiber layer constituting a skin contact surface layer and a crimped fiber layer laminated on a non-skin surface side, and is embossed into a concavo-convex shape formed of many raised parts protruding to a skin side. Thus, since the permeable front surface sheet contains the crimped fiber layer, the raised parts are pronouncedly elevated on a skin side, and the permeable front surface sheet provides substantial cushioning. Further, due to the crimped fiber layer, the embossed concavo-convex shape of the permeable front surface sheet is resistant to collapse even when exposed to body pressure, and a distinctly irregular front surface having excellent skin touch feeling and cushioning property is provided.

The crimped fiber layer does not come into contact with the skin and the touch feeling of the front surface sheet upon contact with and even rubbing of the skin is smooth because the fine fiber layer that constitutes a skin contact surface layer is provided overlying the crimped fiber layer and the fine fiber layer is constituted of fine fibers having the fineness of less than 2.0 dtex.

Further, by constituting the crimped fiber layer of crimped fibers having the fineness of from 3.0 to 5.0 dtex, as shown by test results that are described below, by providing, on a non-skin surface side of the fine fiber layer, a fiber layer of fibers having the fineness larger than that of the fine fiber layer and which are crimped, preferably by heating, the sensory performance such as the skin touch feeling and the uneven feeling and an absorption performance minimizing the return amount of body fluid (i.e., leakage of absorbed body fluid from the absorber) can be provided in a balanced manner.

As the second aspect of the invention, in the absorbent article of the first aspect the hydrophilic sheet is made of fibers having the fineness of from greater than 3.0 dtex to 6.0 dtex.

In the second aspect of the invention, by using fibers a little thicker than the fibers constituting the skin contact surface of the permeable front surface sheet, namely, of the fineness of from greater than 3.0 dtex to 6.0 dtex as the hydrophilic sheet, voids are substantially formed between the fibers, and body fluid is easily transferred through the voids to the absorber. Thus, a liquid residue does not accumulate on the front surface of the absorbent article so that it is dry to the touch.

As a third aspect of the invention, in the absorbent article of the first or second aspect, a hydrophilizing agent is coated on the fibers that constitute the permeable front surface sheet and the second sheet, and strength of durability of the hydrophilizing agent has the relationship of fine fiber layer-≤crimped fiber layer<hydrophilic sheet.

In the third aspect of the invention, in the case where each of the permeable front surface sheet (fine fiber layer and crimped fiber layer) and the hydrophilic sheet is imparted with hydrophilicity by coating a hydrophilizing agent on the fiber, by providing that the strength of the durability of the hydrophilizing agent satisfies a predetermined relationship, the body fluid is easily moved to the absorber, and the body fluid absorbed by the absorber is prevented from leaking out, i.e., the dry to the touch feeling of the front surface side is improved.

As was described above, according to the present invention, there are provided a resilient, durable concavo-convex shape made by a surface embossing process, excellent skin touch and uneven feeling, and excellent absorption performance.

BRIEF DESCRIPTION OF THE DRAWINGS

FIG. 1 is a partially broken perspective view of an absorbent article 1, such as a sanitary napkin according to the present invention.

FIG. 2 is a cross-sectional view of a permeable front surface sheet 3 and a hydrophilic sheet 6.

FIG. 3 is a side view of a manufacturing apparatus 20 of the permeable front surface sheet 3 and hydrophilic sheet 6.

FIG. 4 is a cross sectional view of segments a first embossing roll 21 and a second embossing roll 22 in engagement.

FIG. 5 is a graph of test results of return amounts of absorbed liquid.

DETAILED DESCRIPTION OF THE INVENTION

Hereinafter, an embodiment of the present invention is described in more detail with reference to the drawings.

(Structure of Sanitary Napkin 1)

An absorbent article 1 is provided for use mainly as a panty liner, sanitary napkin, vaginal discharge sheet, incontinence pad and the like and has a structure in which, as shown, for instance, in FIG. 1, an absorber 4 is disposed between an impermeable back surface sheet 2 and a permeable front surface (hereinafter, simply referred to also as a surface sheet), a hydrophilic sheet 6 is disposed between the permeable front surface sheet 3 and the absorber 4. The absorber 4 is surrounded by a crepe paper 5. Around the periphery of the absorber 4, the impermeable back surface sheet 2 and the front surface sheet 3 are joined by adhering means such as a hot-melt adhesive or the like. It should be noted that as long as the absorbent article 1 according to the present invention includes at least the permeable front surface sheet 3 and the hydrophilic sheet 6 according to the invention, absorbent articles of the invention may be in any of many well-known forms such as one provided with a side nonwoven fabric along a longitudinal direction of each of both side parts on a skin surface side or one provided with a wing-like flap fixed so as to engulf a crotch part of underwear (e.g., panties or underpants) during wearing on each of both side parts.

For the impermeable back surface sheet 2, a sheet material having at least water shieldability such as polyethylene, polypropylene or the like can be used. However, other than these, a nonwoven fabric in which impermeability is substantially secured by interposing a water-proof film (in this case, the impermeable back surface sheet is formed with the water-proof film and the nonwoven fabric) and the like can be used. In recent years, there is a tendency to preferably use a sheet material having moisture permeability from the viewpoint of dampness prevention. As the water-shielding and permeable sheet material, a microporous sheet obtained by stretching a sheet uniaxially or biaxially after the sheet is molded by melt-kneading an inorganic filler in an olefinic resin such as polyethylene or polypropylene can be suitably used.

The front surface sheet 3, as shown in FIG. 2, is a multilayered sheet that has a fine fiber layer 3A constituting at least a skin contact surface layer and a crimped fiber layer 3B laminated to the fine fiber layer 3A and that is embossed into a concavo-convex shape formed of many raised parts 7, 7 . . . protruding to a skin side. It should be noted that the front surface sheet 3 is more specifically described below.

The absorber 4 that is interposed between the impermeable back surface sheet 2 and the permeable front surface sheet 3 is made of, for example, a fluff-like pulp and a superabsorbent polymer. As the superabsorbent polymer, a superabsorbent polymer granular powder (SAP) or a superabsorbent polymer fiber (SAF) may be used. As the pulp, a chemical pulp obtained from wood, cellulose fibers such as dissolving pulp and synthetic cellulose fibers such as rayon and acetate can be used. A softwood pulp having a fiber length longer than that of a hardwood pulp is preferably used from the viewpoint of function and price. According to a manufacturing method of the absorber 4, the absorber 4 may be desirably formed into a fiber stacking pulp so as to be highly flexible but may be formed into an air-laid absorber of which volume can be reduced.

A requirement for the hydrophilic sheet 6 disposed between the permeable front surface sheet 3 and the absorber 4 is that it be hydrophilic because body fluids are hydrophilic. Recycled fibers such as rayon, cupra, or the like, or natural fibers such as cotton or the likehaving a hydrophilic property in the raw material itself can be used, or fibers to which a hydrophilic property is imparted by surface treating synthetic fibers such as olefin-based fibers such as polyethylene or polypropylene, polyester-based fibers, or polyamide-based fibers with a hydrophilizing agent can be used. The latter are preferably used.

(Structure of Front Surface Sheet 3)

The front surface sheet 3 includes, as shown in FIG. 2, a two-layered structure that is made of a fine fiber layer 3A constituting a skin contact surface layer and a crimped fiber layer 3B laminated to the fine fiber layer 3A and that is embossed into a concavo-convex shape formed of many elevated parts 7, 7 . . . protruding to a skin side.

As fibers that constitutes the fine fiber layer 3A, fine fibers having the fineness of less than 2.0 dtex, preferably of about more than 1.1 dtex and less than 2.0 dtex are used. When the fine fiber having the fineness in this range is used, the skin touch feeling is soft, the rubbing feeling (friction with the skin) is reduced, and the absorption performance is excellent.

As the fibers that constitute the fine fiber layer 3A, for example, other than synthetic fibers such as olefin based fibers such as polyethylene or polypropylene, polyester based fibers, and polyamide based fibers, recycled fibers such as rayon and cupra, and natural fibers such as cotton can be used, and a nonwoven fabric obtained according to an appropriate processing method such as an air-through method, a spun lace method, a spun bond method, a thermal bond method, a melt blown method, a needle punch method or the like can be used. Among these processing methods, the spun lace method is excellent in flexibility of the nonwoven fabric, the spun bond method is excellent in drape of the nonwoven fabric, and the air-through method and the thermal bond method are excellent in a bulk and softness of the nonwoven fabric. Fibers of the nonwoven fabric may be either a long or short. However, short fibers are preferably used to exhibit texture like that of toweling. Further, an olefin-base fiber such as polyethylene or polypropylene having a relatively low melting point is preferably used to make it easy to apply an embossing process. Still further, a composite fiber such as a core/sheath type fiber in which a fiber having a high melting point is used as a core and a fiber having a low melting point is used as a sheath, a side-by-side type fiber, a divided type fiber or the like can be preferably used.

As fibers to be crimped for the crimped fiber layer 3B, in order to impart crimpability it is preferable to use synthetic fibers having a core-sheath structure, namely synthetic fibers having different heat shrinkage temperatures as a core and a sheath, the core being eccentric with respect to a sheath, and the fiber being three-dimensionally crimped by heat treatment. In particular, it is preferable to use polyethylene terephthalate (PET) having a melting point of about 255° C. as the core, and polyethylene (PE) having a melting point of from about 95 to 140° C. as the sheath. By using PET, which has greater stiffness than other fibers as the core, the stiffness of the crimped fiber layer 3B is increased, low stiffness of the fiber layer 3A is compensated for, resulting by and shape retention of the concavo-convex shape of the front surface sheet 3 being particularly excellent. Alternatively, as the fibers to be crimped for the crimped fiber layer 3B, side-by-side composite fibers obtained by adhering synthetic resins having different heat shrinkage temperatures can be by heat treating, or have a zigzag crimp or a spiral crimp imparted thereto by stretching.

Due to the fibers being crimped, the crimped fiber layer 3B is bulky and exhibits substantial stiffness. Therefore, even though the fine fiber layer 3A is soft, the front surface sheet 3 retains firmly the concavo-convex shape produced by embossing, the cushioning due to the concavo-convex shape is retained even when exposed to body pressure. Therefore, the front surface sheet is comfortable against the skin due to the smoothness and softness of the fine fiber layer 3A, and contact area with the skin is continually reduced due to retention of the concavo-convex shape.

The fibers that constitute the crimped fiber layer 3B, are less fine than the fibers of the fine fiber layer 3A. Specifically, the fineness of the crimped fibers is from 3.0 to 5.0 dtex, preferably from about 3.0 to 4.5 dtex. Because fibers less fine than the fibers of the fine fiber layer 3A are used, shape retention of the concavo-convex shape of the permeable front surface sheet 3 is excellent, the cushion property can be more surely retained, and absorption performance of the body fluid is excellent, which is described hereinafter in the examples.

The fibers that constitute the hydrophilic sheet 6, are of fineness of from greater than 3.0 dtex to 6.0 dtex, preferably of about from greater than 3.0 dtex to 4.0 dtex. Because a little thicker fiber, preferably fibers less fine than the fibers constituting the permeable front surface sheet 3 are used, gaps are present between the fibers through which body fluid that passed through the permeable front surface sheet 3 readily passes to the absorber 4. Therefore, liquid does not accumulate on the front surface of the absorbent article so that it is dry to the touch.

It should be noted that the relationship of the finenesses of the raw material fibers that constitute the front surface sheet 3 (fine fiber layer 3A and crimped fiber layer 3B) and the hydrophilic sheet 6, expressed as dtex number, preferably satisfies fine fiber layer 3A<crimped fiber layer 3B<hydrophilic sheet 6. Namely, the fibers of the fine fiber layer 3A are finer than the fibers of the crimped fiber layer 3B which are, in turn, are finer than the fibers of the second sheet 6. When a fineness gradient in which the dtex number becomes higher toward the absorber 4 is provided and the gaps between the fibers are thereby gradually larger, the body fluid is rapidly transferred to the absorber 4.

To emboss the permeable front surface sheet 3, apparatus 20, as shown in FIGS. 3 and 4, is preferably used, in which are provided a first embossing roll 21 on which many projections 21a, 21a . . . are arranged and a second embossing roll 22 on which many recesses 22a, 22a . . . are formed corresponding to the projected parts 21a. When the front surface sheet 3 in which the fine fiber layer 3A and the crimped fiber layer 3B are laminated is passed between the first embossing roll 21 and the second embossing roll 22, by engagement of the fine fiber layer with the projections 21a and the recesses with the crimpled fiber layer 3B, an emboss pattern is imparted.

After that, by passing the hydrophilic sheet 6 transferred from a separate path between the second embossing roll 22 and a flat roll 23 together with the front surface sheet 3, the front surface sheet 3 and the hydrophilic sheet 6 are joined and integrated (laminated together). For joining these, a hot-melt adhesive or the like is coated on surfaces of raised parts 7 of the crimped fiber layer 3B of the front surface sheet 3 at least at the highest areas corresponding to the projections 22b of the second embossing roll 22 and the front surface sheet 3 and the hydrophilic sheet 6 are thereby adhered, or the projections 22b of the second embossing roll 22 are heated to melt surfaces of the crimped fibers at the raised parts 7 of the crimped fiber layer, 3B and the front surface sheet 3 and the hydrophilic sheet 6 are thereby heat-sealed.

In order to more form a more highly defined or deeper concavo-convex shape by embossing, an aperture 22c is formed at the bottom of each recess 22a of the embossing roll 22, and by vacuum suctioning from the aperture 22c during engagement of the front surface sheet between the projections 21a and the recesses 22a to generate a negative pressure, the front surface sheet 3 is more deeply and completely drawn into recesses and thereby deformed to conform to the shape of the recesser.

When the concavo-convex shape is imparted to the front surface sheet 3 by using the manufacturing apparatus 20, as shown in FIG. 2, the front surface sheet 3 is formed into many raised parts 7 bulging on a skin side, and voids are thereby formed between the front surface sheet 3 and the hydrophilic sheet 6 at the elevated parts 3a. Cushioning of the front surface sheet 3 is thereby increased and the shape of the elevated parts 3a resist deformation. Moreover, even if the absorbent article is exposed to body pressure that may collapse the space, the considerable stiffness of the crimped fibers provides resiliency for returning the front surface sheet to its initial form and, moreover, augments the cushioning property.

All of the fibers that constitute the front surface sheet 3 (fine fiber layer 3A and crimped fiber layer 3B) and the hydrophilic sheet 6 are preferably hydrophobic fibers coated with a hydrophilizing agent, and the strength of the durability of the hydrophilizing agent at is preferably constituted so as to satisfy the relationship of fine fiber layer 3A≤crimped fiber layer 3B<hydrophilic sheet 6. The strength of the durability of the hydrophilizing agent means how well the hydrophilizing agent is fixed to the fibers without being washed away together with the liquid (body fluid) during liquid passage, and weak durability means that the hydrophilizing agent is not likely to be washed away together with the liquid during liquid passage.

As the hydrophilizing agent, for example, an anionic surfactant, a carboxylate, an acylated hydrolyzed protein, a sulfonate, a sulfuric acid ester salt, a phosphoric acid ester salt, a nonionic surfactant, a polyoxyethylene base surfactant, a carboxylic acid ester, carboxylic acid amide, a polyalkylene oxide block copolymer, a cationic surfactant, a quaternary ammonium salt, an amphoteric surfactant, an imidazolium derivative or the like can be used. Other than these, any hydrophilizing agent known to be coatable on fibers may be applied.

As a coating method of the hydrophilizing agent, for example, coating by spraying, coating by gravure printing or flexo printing, or curtain coating by various coaters can be used. Further, the hydrophilizing agent may be kneaded into the fibers, for example by kneading into synthetic fibers raw material. The hydrophilicity can be controlled by controlling a coating amount of the hydrophilizing agent. In order to make the body fluid readily infiltrate to the absorber 4 side, the hydrophilicity is preferably controlled such that the relationship of durability of hydrophilicity fine fiber layer 3A≤crimped fiber layer 3B<hydrophilic sheet 6 may be satisfied.

Further, the durability of the hydrophilizing agent can be controlled, by adjusting amounts of agents, such as adhesive resins or catalysts which enhance fixation of the hydrophilizing agents to the fibers, for example, acrylic aqueous resins, gum-based latex, urethane resins, polyester-based resins, polyvinyl resins.

When the strength of the durability of the hydrophilizing agent on the front surface is attenuated, the affinity with the fiber of the hydrophilizing agent on the front surface is decreased, so that the hydrophilizing agent attached to the fibers is washed away together with the body fluid upon a single discharge of body fluid, leaving the fibers in their untreated hydrophobic state. At this time, because the fine fiber layer 3A, (the skin contact surface layer) has become hydrophobic or substantially hydrophobic if residual hydrophilizing agent remains, flow of the body fluid to the absorber 4 side is facilitated, the body fluid absorbed by the absorber 4 tends not to leak out from the absorber 4 due to water-repellent action of the hydrophobic fibers, and the front surface stays substantially dry to the touch.

EXAMPLES

In order to perform a sensory evaluation of the skin touch feeling and the uneven feeling and an absorption performance evaluation of the return amount of the body fluid (i.e., how much absorbed body fluid leaks out of the absorber) of the present sanitary napkin, the following tests were carried out.

Specifications of the sanitary napkins used in the test and the results are as shown in Table 1 and FIG. 5.

TABLE 1

| | | Example 1 | Example 2 | Comparative Example 1 | Comparative Example 2 |
|---|---|---|---|---|---|
| Specification of permeable top sheet 3 | | colspan Air-through 25 gsm | | | |
| Specification of thin fiber layer 3A | Basis weight (gsm) | | 10 | | |
| | Kind | | PP/PE (concentric core type) | | |
| | Fineness (dtex) | 1.4 | 1.1 | 1.1 | 1.1 |
| Specification of crimped fiber layer 3B | Basis weight (gsm) | | 15 | | |
| | Kind | | PP/PE (eccentric core type) | | |
| | Fineness (dtex) | 3.3 | 3.3 | 2.4 | 5.6 |
| Specification of second sheet 6 | | | Air-through 18 gsm PP/PE, 5.6 dtex | | |
| Specification of absorber 4 | | | Air-laid | | |
| Sensory performance | Touch feeling | Excellent | Good | Good | Poor |
| | Uneven feeling | Good | Good | Poor | Good |
| Absorption performance | Result of absorption performance evaluation | Good | Poor | Bad | Poor |
| | Return amount (g) | 0.083 | 0.133 | 0.278 | 0.111 |

As an evaluation method of the skin touch feeling, subjects relatively evaluated the touch feeling when a surface of each of the above-described 4 samples was touched with a hand. As the uneven feeling, an appearance of an apparent concavo-convex state of a front surface was relatively evaluated for each of the above-described 4 samples. Regarding evaluation criteria of the skin touch feeling among the 4 samples, a sample that was determined to be most excellent by 4 or more subjects among 10 subjects was denoted as excellent, a sample that was determined to be most excellent by 2 or more and 3 or fewer subjects was denoted as good, a sample that was determined to be most excellent by one subject was denoted as poor, and a sample that was determined to be most excellent by no subject was denoted as bad. Regarding the return amount, 1 cc of artificial menstrual blood at 37° C. was injected, after an interval of 3 minutes, 1 cc of the artificial menstrual blood at 37° C. was injected at the same place once again, after an interval of 1 minute, a top surface thereof was covered with a filter paper upon which a weight of 5 g/cm$^2$ was disposed for 5 minutes, and a change of weight of the filter paper was measured as the return amount. The artificial menstrual blood contained, in 1 L, 100 ml of glycerin, 4.6 g of CMC (sodium carboxymethylcellulose), 875 ml of purified water, 10 g of sodium chloride, and 10.7 g of sodium carbonate.

As the result, according to the sensory evaluation such as the skin touch feeling and uneven feeling, it was shown, as shown in Table 1, that the sample having the fineness of the crimped fiber layer 3B of 3.3 dtex was most excellent. Further, according to the absorption performance evaluation regarding the return amount of the body fluid, it was shown, as shown in FIG. 5, that the return amount had a minimum value in the neighborhood of 4.5 dtex of the fineness of the crimped fiber layer 3B. From these results, the crimped fiber layer 3B having the fineness of from 3.0 to 5.0 dtex has excellent sensory performance such as the skin touch feeling and the uneven feeling and has excellent absorption performance in which the return amount of the body fluid is low. That is, an absorbent article of the invention incorporating fibers of the hereabove specified fineness combines the sensory performance and the absorption performance in a particularly good balance. Further, if the crimped fiber layer 3B having the fineness of from 3.0 to 4.5 dtex is used, where the return amount is in the neighborhood of the minimum value and the skin touch feeling and the uneven feeling are excellent, such absorbent articles of the invention are even more preferable.

Further, in the comparison of Example 1 and Example 2, when the fineness of the fine fiber layer 3A was changed from 1.4 dtex to 1.1 dtex, while the sensory performance maintained a substantially excellent state, the absorption performance was slightly deteriorated because the return amount increased from 0.083 g to 0.133 g. Therefore, the fineness of the fine fiber layer 3A is preferably less than 2.0 dtex and greater than 1.1 dtex.

Example of Other Forms (1) In the above, the permeable front surface sheet 3 was formed into the two-layered structure that was made of the fine fiber layer 3A constituting the skin contact surface layer and the crimped fiber layer 3B laminated on the non-skin surface side of the fine fiber layer 3A. However, a composite layer sheet of a three-layered structure or more obtained by laminating other sheet material on the non-skin surface side of the crimped fiber layer may be formed according to the invention.

(2) In the above, while the permeable front surface layer 3 was formed into the composite layer structure made of the fine fiber layer 3A and the crimped fiber layer 3B, by mixing the fine fibers of the fineness of less than 2.0 dtex hereabove specified for the fine fiber 3A with the crimped fibers hereabove specified for the crimped fiber layer 3B, a structure of one layer may be used. Thus, while the shape retention of the concavo-convex shape due to the embossing process is deteriorated compared with the composite layer structure, since fiber density of the front surface becomes lower due to the pressure of the crimped fibers on the front surface, the absorptivity of the body fluid becomes higher and the liquid migrates from the front surface more quickly and thoroughly. A mixing ratio is preferably set to fibers of the fine fiber layer 3A: fibers of the crimped fiber layer 3B=3:7 to 7:3.

The invention claimed is:

1. An absorbent article comprising:
   an absorber interposed between a permeable front surface sheet and a back surface sheet; and
   a hydrophilic sheet consisting of one fiber layer and disposed between the permeable front surface sheet and the absorber, wherein:
   the permeable front surface sheet is a laminate structure of a fine fiber layer made of fine fibers and that constitutes a skin contact surface layer, the fine fibers having a fineness of less than 2.0 dtex, and a crimped fiber layer made of crimped fibers and that is laminated on a non-skin contact surface of the fine fiber layer, the crimped fibers having a fineness of from 3.0 to 5.0 dtex, and the permeable front surface sheet is embossed into a concavo-convex shape formed of a multiplicity of convex parts of the fine fiber layer protruding to a skin side and a multiplicity of convex parts of the crimped fiber layer protruding toward the fine fiber layer, wherein top portions of the convex parts of the crimped fiber layer protruding toward the fine fiber layer are adhered to the fine fiber layer by applying hot-melt adhesive or by melting the crimped fiber layer and wherein spaces are formed between raised portions of the permeable front surface sheet protruding away from the hydrophilic sheet and the hydrophilic sheet;
   the hydrophilic sheet is the only fiber layer interposed between the permeable front surface sheet and the absorber,
   the hydrophilic sheet is made of a fiber having fineness of from greater than 3.0 dtex to 6.0 dtex;
   the fineness of the fibers, expressed as dtex number, that constitute the front surface sheet and the hydrophilic sheet have a relationship of fine fiber layer<crimped fiber layer<hydrophilic layer; and
   each of the fibers that constitute the front surface sheet and the hydrophilic sheet is a hydrophobic fiber coated with a hydrophilizing agent and durability of the hydrophilizing agent has a relationship of the fine fiber layer≤the crimped fiber layer<the hydrophilic sheet.

* * * * *